United States Patent
Hashimoto et al.

(10) Patent No.: US 10,954,196 B2
(45) Date of Patent: Mar. 23, 2021

(54) METHOD FOR PRODUCING 5-HYDROXY-1H-IMIDAZOLE-4 CARBOXAMIDE 3/4 HYDRATE

(71) Applicant: FUJIFILM Corporation, Tokyo (JP)

(72) Inventors: Tomohiro Hashimoto, Toyama (JP); Yuta Kobayashi, Toyama (JP); Yuichi Fukatsu, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/858,089

(22) Filed: Apr. 24, 2020

(65) Prior Publication Data

US 2020/0247759 A1    Aug. 6, 2020

Related U.S. Application Data

(63) Continuation of application No. PCT/JP2018/039374, filed on Oct. 23, 2018.

(30) Foreign Application Priority Data

Oct. 27, 2017 (JP) .............................. JP2017-208570

(51) Int. Cl.
    *C07D 233/90*    (2006.01)
(52) U.S. Cl.
    CPC ................................. *C07D 233/90* (2013.01)
(58) Field of Classification Search
    CPC .................................................. C07D 233/90
    See application file for complete search history.

(56) References Cited

U.S. PATENT DOCUMENTS

| | | | | |
|---|---|---|---|---|
| 9,108,928 B2* | 8/2015 | Fujimoto | ................. | A61P 35/00 |
| 9,248,102 B2* | 2/2016 | Yamasaki | ............. | A61K 9/2095 |
| 9,567,303 B2* | 2/2017 | Fujimoto | ............. | C07D 233/90 |
| 2010/0210855 A1 | 8/2010 | Nobuo et al. | | |
| 2014/0275568 A1* | 9/2014 | Fujimoto | ........... | A61K 31/4164 |
| | | | | 548/323.1 |

FOREIGN PATENT DOCUMENTS

| | | |
|---|---|---|
| EP | 0051962 A2 | 5/1982 |
| EP | 0 159 777 A1 | 10/1985 |
| EP | 2762469 A1 | 8/2014 |
| JP | 58-024569 A | 2/1983 |
| JP | 60-185727 A | 9/1985 |
| WO | 2009/035168 A1 | 3/2009 |
| WO | 2013/047758 A1 | 4/2013 |

OTHER PUBLICATIONS

Miller et al., "Substituted Imidazoles as Precursors of the Purines", Journal of the American Chemical Society, vol. 74, pp. 2892-2894, 1952 (3 pages total).
Kondo et al., "Development of therapeutic agent for myelodysplastic syndrome, 4-carbamoyl-imidazolium-5-olate(MBR-108)", Lecture abstracts IV of the 90th spring annual conference of the Chemical Society of Japan, pp. 1529, 2010 (3 pages total).
Kondo et al., "Synthesis of 4-carbamoyl-imidazolium-5-olate not having coloring material", Lecture abstracts II of the 88th spring annual conference of the Chemical Society of Japan, pp. 1238, 2008 (5 pages total).
International Search Report dated Jan. 8, 2019 in International Application No. PCT/JP2018/039374.
Written Opinion of the International Searching Authority dated Jan. 8, 2019 in International Application No. PCT/JP2018/039374.
International Preliminary Report on Patentability dated Apr. 28, 2020 in International Application No. PCT/JP2018/039374.
Extended European Search Report dated Jun. 23, 2020 in European Application No. 18870511.5.
Office Action dated Feb. 9, 2021 in Japanese Application No. 2019-551163; 7 pages total.

* cited by examiner

*Primary Examiner* — Matthew P Coughlin
(74) *Attorney, Agent, or Firm* — Sughrue Mion, PLLC (57) ABSTRACT

Provided are a method for producing a 5-hydroxy-1H-imidazole-4-carboxamide•¾ hydrate, including reacting an acidic salt of 5-hydroxy-1H-imidazole-4-carboxamide or a hydrate thereof with a base selected from the group consisting of a phosphate and an amino acid in the presence of an acidic solvent to obtain a 5-hydroxy-1H-imidazole-4-carboxamide•¾ hydrate; and a 5-hydroxy-1H-imidazole-4-carboxamide•¾ hydrate obtained by the production method.

11 Claims, 2 Drawing Sheets

METHOD FOR PRODUCING 5-HYDROXY-1H-IMIDAZOLE-4 CARBOXAMIDE 3/4 HYDRATE

CROSS-REFERENCE TO RELATED APPLICATIONS

This application is a continuation application of International Application No. PCT/JP2018/039374, filed Oct. 23, 2018, which is incorporated herein by reference. Further, this application claims priority from Japanese Patent Application No. 2017-208570, filed Oct. 27, 2017, which is incorporated herein by reference.

BACKGROUND OF THE INVENTION

1. Field of the Invention

The present invention relates to a method for producing 5-hydroxy-1H-imidazole-4-carboxamide ¾ hydrate.

2. Description of the Related Art

5-Hydroxy-1H-imidazole-4-carboxamide (hereinafter, also referred to as "compound A") is a compound useful as an anticancer agent (for example, see WO2009/035168A).

The compound A is produced, for example, from 2-aminomalonamide (see, for example, WO2009/035168A, JP1983-024569A (JP-S58-24569A), WO2013/047758A, and Journal of American Chemical Society (J. Am. Chem. Soc.), Vol. 74, pp. 2892 to 2894, 1952).

Journal of American Chemical Society (J. Am. Chem. Soc.), Vol. 74, pp. 2892 to 2894, 1952 discloses that the compound A can be obtained by reacting 2-aminomalonamide with ethyl formimidate. However, this production method has a low yield and is therefore not satisfactory.

WO2009/035168A discloses that benzenesulfonate of the compound A can be obtained by reacting benzenesulfonate of 2-aminomalonamide with trimethyl orthoformate in the presence of benzenesulfonic acid. Furthermore, it is disclosed that the compound A can be obtained by neutralizing the benzenesulfonate of the compound A with sodium hydrogen carbonate.

However, this production method has drawbacks such as the formation of genotoxic benzenesulfonic acid ester and the necessity of a large excess of trimethyl orthoformate. Therefore, this production method cannot be said to be an industrially excellent production method. Further, the obtained compound A is colored and therefore has poor coloring stability during storage. In Test Example 1 and Test Example 2 of WO2009/035168A, it is disclosed that the sulfonate of the compound A and the hydrochloride of the compound A were stable, but the compound A has changed color to indigo blue or blue. Further, WO2009/035168A discloses that, in order to obtain the compound A having excellent coloring stability during storage, it is necessary to make the compound A contain a trace amount of acid. In addition, Example 6 of WO2009/035168A discloses the compound A containing about 2.5% of benzoic acid.

JP1983-024569A (JP-S58-24569A) discloses that a crude crystal of the compound A can be obtained by reacting 2-aminomalonamide with triethyl orthoformate in the presence of sulfuric acid. However, this production method has drawbacks such as the necessity of a large excess of triethyl orthoformate and the necessity of a large amount of activated carbon. Therefore, this production method cannot be said to be an industrially excellent production method.

Further, JP1983-024569A (JP-S58-24569A) discloses that the compound A can be obtained by reacting the crude crystal of the compound A with an acid and then neutralizing the resulting reaction product with ammonia.

WO2013/047758A discloses the following production method. 2-Aminomalonamide is reacted with a compound in the presence of a carboxylic acid to give the compound A. The obtained compound A is reacted with an acidic compound to obtain an acidic salt of the compound A or a hydrate thereof. Further, the acidic salt of the compound A or the hydrate thereof thus obtained is reacted with a salt in the presence of an acidic solvent to obtain a compound A•¾ hydrate.

It is known that, in the formulation of the compound A, blue coloring can be prevented by including an acidic substance (for example, see JP1985-185727A (JP-S60-185727A). JP1985-185727A (JP-S60-185727A) discloses that "The present compound itself has a property of being colored by oxygen, heat, light, or the like. For example, in a case where the present compound is applied to an oral preparation, the compound is likely to be affected by the interaction of coexisting excipients and to exhibit more remarkable coloring in a more complicated reaction route."

Heretofore, it has been considered that the compound A is colored blue and has a problem in coloring stability during storage. In order to obtain the compound A having excellent coloring stability during storage, it was said that (1) production of an acidic salt of the compound A, (2) coexistence of an acidic substance, or (3) inclusion of a trace amount of an acidic substance was required.

In addition, WO2013/047758A discloses a method for producing a compound A•¾ hydrate which improves these problems and has excellent coloring stability during storage without using an additive in combination.

SUMMARY OF THE INVENTION

There is a strong demand for a method for producing a compound A•¾ hydrate that has high purity, a very small color difference between before and after storage, and excellent coloring stability during long-term storage.

In addition, it has been found in the production method of WO2013/047758A that, in a case where the solvent used for the crystallization in the final step remains in the compound A•¾ hydrate, the coloring stability of the compound during storage is lower than in a case where the solvent is completely removed.

There is a demand for a method for producing a compound A•¾ hydrate in which the compound is less likely to be colored even in a case where the solvent used for the crystallization in the final step remains in the compound A•¾ hydrate, and the washing load can be reduced.

As a result of intensive studies under such circumstances, the present inventors have found the following [1] to [12] and completed the present invention. Specific means for achieving the above object are as follows.

[1] A method for producing a 5-hydroxy-1H-imidazole-4-carboxamide•¾ hydrate, comprising:
reacting an acidic salt of 5-hydroxy-1H-imidazole-4-carboxamide or a hydrate thereof with a base selected from the group consisting of a phosphate and an amino acid in the presence of an acidic solvent to obtain a 5-hydroxy-1H-imidazole-4-carboxamide•¾ hydrate.

[2] The production method according to [1], in which the base is a phosphate.

[3] The production method according to [1], in which the base is an alkali metal salt of phosphoric acid.

[4] The production method according to [1], in which the base is dipotassium hydrogen phosphate.

[5] The production method according to [1], in which the base is an amino acid.

[6] The production method according to [1], in which the base is an amino acid selected from the group consisting of an acidic amino acid and a neutral amino acid.

[7] The production method according to [1], in which the base is a neutral amino acid.

[8] The production method according to [1], in which the base is serine, alanine, β-alanine, threonine, glycine, or cysteine.

[9] The production method according to [1], in which the base is alanine, β-alanine, threonine, or cysteine.

[10] The production method according to any one of [1] to [9], in which the acidic salt is a hydrate of a hydrochloride.

[11] The production method according to any one of [1] to [10], in which the acidic solvent is hydrochloric acid.

[12] A 5-hydroxy-1H-imidazole-4-carboxamide•¾ hydrate obtained by the production method according to any one of [1] to [11].

According to the present invention, there is provided a method for producing a compound A•¾ hydrate that has high purity, a very small color difference between before and after storage, and excellent coloring stability during long-term storage.

Further, according to the present invention, there is provided a method for producing a compound A•¾ hydrate in which the compound is less likely to be colored even in a case where the solvent used for the crystallization in the final step remains in the compound A•¾ hydrate, and the washing load can be reduced.

DESCRIPTION OF THE PREFERRED EMBODIMENTS

The present invention will be described in detail below. In the present specification, a numerical range indicated by using "to" indicates a range including numerical values described before and after "to" as a minimum value and a maximum value, respectively.

Further, in the present specification, in a case where a plurality of substances corresponding to components are present in the composition, the amount of each component in the composition means a total amount of the plurality of substances present in the composition, unless otherwise specified.

In the present specification, the following terms are defined as follows unless otherwise specified.

The $C_{1-3}$ alkyl group means a methyl group, an ethyl group, a propyl group, or an isopropyl group.

The halogenated hydrocarbon means methylene chloride, chloroform, or dichloroethane.

The alcohol means a $C_{1-6}$ alcohol such as methanol, ethanol, propanol, 2-propanol, butanol, or 2-methyl-2-propanol.

The ether means diethyl ether, diisopropyl ether, dioxane, tetrahydrofuran, anisole, ethylene glycol dimethyl ether, diethylene glycol dimethyl ether, or diethylene glycol diethyl ether.

The ketone means a $C_{1-6}$ ketone such as acetone, 2-butanone, or 4-methyl-2-pentanone.

The ester means $C_{1-3}$ alkyl of a $C_{1-6}$ carboxylic acid such as methyl acetate, ethyl acetate, propyl acetate, or butyl acetate.

The amide means N,N-dimethylformamide, N,N-dimethylacetamide, 1-methyl-2-pyrrolidone, or the like.

The alkali metal salt means a lithium salt, a sodium salt, a potassium salt, or the like.

The amino acid includes amino acids such as α-amino acid, β-amino acid, γ-amino acid, and δ-amino acid, and means a neutral amino acid, an acidic amino acid, or a basic amino acid. In addition, the amino acid means a D-form, L-form, or D/L-form amino acid.

Examples of the neutral amino acid include an amino acid having an alkyl group in the side chain, such as glycine, alanine, β-alanine, valine, leucine, or isoleucine; an amino acid having a hydroxy group in the side chain, such as serine or threonine; an amino acid containing sulfur in the side chain, such as cysteine or methionine; an amino acid having an amide group in the side chain, such as asparagine or glutamine; an amino acid having an imino group in the side chain, such as proline or hydroxyproline; and an amino acid having a phenyl group in the side chain, such as phenylalanine, tyrosine, or tryptophan.

The acidic amino acid means an amino acid having an acidic side chain, such as aspartic acid or glutamic acid.

The basic amino acid means an amino acid having a basic side chain, such as lysine, arginine, or histidine.

<Production Method According to Embodiment of Present Invention>

The production method according to the embodiment of the present invention includes a step of reacting an acidic salt of compound A or a hydrate thereof with a base selected from the group consisting of a phosphate and an amino acid in the presence of an acidic solvent to obtain a compound A•¾ hydrate, and, if necessary, post-treatment steps such as filtration, washing, and drying, and/or other steps.

The compound A•¾ hydrate obtained by the production method according to the embodiment of the present invention has characteristics such as excellent coloring stability during storage and high purity.

Furthermore, the compound A•¾ hydrate obtained by the production method according to the embodiment of the present invention has a feature that the compound is less likely to be colored even in a case where the solvent used for the crystallization in the final step remains.

That is, the production method according to the embodiment of the present invention is useful as an industrial production method of the compound A•¾ hydrate used as a pharmaceutical.

<Compound A•¾ Hydrate>

The compound A•¾ hydrate obtained by the production method according to the embodiment of the present invention is preferably colorless or slightly yellow, and more preferably colorless.

The compound A•¾ hydrate of the present invention preferably has a color difference (ΔE) of 6 or less from that before storage after storage for 5 days under the conditions of 60° C. and 75% relative humidity, and more preferably a color difference (ΔE) of 3 or less from that before storage after storage for 5 days under the conditions of 60° C. and 75% relative humidity.

The color difference of the compound A•¾ hydrate of the present invention is measured by a reflection method using a spectrophotometric color difference meter.

The purity of the compound A•¾ hydrate of the present invention is preferably 99.9% or more, and in a case where HPLC analysis is carried out under the conditions of Test Example 2, it is preferable that a component having a retention time of 27.0 minutes is not detected.

Next, the production method according to the embodiment of the present invention will be described.

The acidic salt of the compound A or the hydrate thereof used in the present application was produced, for example, by the method disclosed in WO2013/047758A.

(Production Method 1)

The compound A•¾ hydrate can be produced by reacting an acidic salt of compound A or a hydrate thereof with a phosphate in the presence of an acidic solvent.

Examples of the acidic solvent include an aqueous solution of a mineral acid. Specific examples of the acidic solvent include hydrochloric acid, sulfuric acid, and nitric acid, among which hydrochloric acid is preferable. By using hydrochloric acid, a uniform compound A•¾ hydrate can be produced under lower temperature conditions.

The amount of the acidic solvent used is not particularly limited, but may be 5 times (v/w) to 50 times (v/w) the amount of the acidic salt of the compound A or the hydrate thereof.

The concentration of the acidic solvent is not particularly limited. For example, in a case where hydrochloric acid is used, the concentration of hydrochloric acid is preferably 0.3 mol/L to 0.8 mol/L and more preferably 0.4 mol/L to 0.5 mol/L.

The phosphate is preferably an alkali metal salt of phosphoric acid, more preferably an alkali metal salt of phosphoric acid having a first acid dissociation constant (hereinafter, also referred to as $pK_{a1}$) of 2 to 4, and still more preferably an alkali metal salt of phosphoric acid having a $pK_{a1}$ of 2 to 3.

Specifically, the phosphate is preferably at least one selected from the group consisting of potassium dihydrogen phosphate, dipotassium hydrogen phosphate, tripotassium phosphate, sodium dihydrogen phosphate, disodium hydrogen phosphate, and trisodium phosphate; more preferably at least one selected from the group consisting of dipotassium hydrogen phosphate, disodium hydrogen phosphate, potassium dihydrogen phosphate, and sodium dihydrogen phosphate, each of which is an alkali metal salt of phosphoric acid having a first acid dissociation constant (pKa1) of 2 to 3; and still more preferably dipotassium hydrogen phosphate.

The amount of the phosphate used can be appropriately selected according to the type of the acidic salt of the compound A or the hydrate thereof, the type of the salt, and the type and concentration of the acidic solvent. For example, it is preferable to adjust the amount of the phosphate used such that the pH of the suspension or solution of the compound A after the addition of the phosphate is 1 to 4, and it is more preferable to adjust the amount of the phosphate used such that the pH is 1.5 to 2.5.

Specifically, in a case where the hydrochloride of the compound A is dissolved in 0.4 mol/L to 0.5 mol/L hydrochloric acid, and then reacted with dipotassium hydrogen phosphate as the alkali metal salt of phosphoric acid, the amount of dipotassium hydrogen phosphate to be used is preferably 0.5- to 2.5-fold molar equivalent and more preferably 0.5- to 1.5-fold molar equivalent, per 1 molar equivalent of the hydrochloride of the compound A.

The acidic salt of the compound A or the hydrate thereof used in the present production method is preferably a hydrate of the acidic salt, more preferably a hydrate of the hydrochloride, and still more preferably a dihydrate of the hydrochloride.

The present production method can also be carried out by adding an alkali metal salt of phosphoric acid to a suspension or solution of the acidic salt of the compound A or the hydrate thereof, and a method in which an alkali metal salt of phosphoric acid is added to the acidic salt solution of the compound A is preferable.

Specifically, the present production method can be carried out in such a manner that the acidic salt of the compound A or the hydrate thereof is added to an acidic solvent, and, if necessary, heated to prepare an acidic salt solution of the compound A, and a phosphate is added to the resulting solution.

The acid and base constituting the alkali metal salt of phosphoric acid used in the present production method may be individually added in the order of the acid and the base to the suspension or solution of the acidic salt of the compound A or the hydrate thereof.

For example, instead of using dipotassium hydrogen phosphate as the alkali metal salt of phosphoric acid, potassium hydroxide or the like may be added after adding phosphoric acid to the suspension or solution of the acidic salt of the compound A or the hydrate thereof.

The reaction temperature in the present production method is preferably 15° C. to 60° C. and more preferably 40° C. to 50° C.

The reaction time in the present production method is, for example, preferably 1 minute to 24 hours and more preferably 30 minutes to 6 hours.

The reaction atmosphere is not particularly limited, but the reaction is preferably carried out in an inert gas atmosphere. Examples of the inert gas atmosphere include an argon atmosphere and a nitrogen atmosphere.

In the present production method, a seed crystal may be added as necessary. The seed crystal may be, for example, a part of a crystal produced in the same manner as in the method described in Example 12 (2) of WO2013/047758A, or may be a part of a crystal produced by the production method according to the embodiment of the present invention.

(Production Method 2)

The compound A•¾ hydrate can be produced by reacting an acidic salt of compound A or a hydrate thereof with an amino acid in the presence of an acidic solvent.

Examples of the acidic solvent include an aqueous solution of a mineral acid. Specific examples of the acidic solvent include hydrochloric acid, sulfuric acid, and nitric acid, among which hydrochloric acid is preferable. By using hydrochloric acid, a uniform compound A•¾ hydrate can be produced under lower temperature conditions.

The amount of the acidic solvent used is not particularly limited, but may be 5 times (v/w) to 50 times (v/w) the amount of the acidic salt of the compound A or the hydrate thereof.

The concentration of the acidic solvent is not particularly limited. For example, in a case where hydrochloric acid is used, the concentration of hydrochloric acid is preferably 0.3 mol/L to 0.8 mol/L, and more preferably 0.4 mol/L to 0.5 mol/L.

The amino acid is preferably an acidic or neutral amino acid, more preferably a neutral amino acid, still more preferably an amino acid having a $pK_{a1}$ of 2 to 4, and even still more preferably an amino acid having a $pK_{a1}$ of 2 to 3.

Specifically, serine, alanine, β-alanine, threonine, glycine, or cysteine is preferable, and alanine, β-alanine, threonine, or cysteine is more preferable.

The amount of the amino acid used can be appropriately selected according to the type of the acidic salt of the compound A or the hydrate thereof, the type of the salt, and the type and concentration of the acidic solvent. For example, it is preferable to adjust the amount of the amino acid used such that the pH of the suspension or solution of the compound A after the addition of the amino acid is 1 to 4, and it is more preferable to adjust the amount of the amino acid used such that the pH is 1.5 to 2.5.

Specifically, in a case where the hydrochloride of the compound A is dissolved in 0.4 mol/L to 0.5 mol/L hydrochloric acid, and then reacted with an amino acid, the amount of the amino acid to be used is preferably 0.5- to 5-fold molar equivalent and more preferably 1.5- to 2.5-fold molar equivalent, per 1 molar equivalent of the hydrochloride of the compound A.

The acidic salt of the compound A or the hydrate thereof used in the present production method is preferably a hydrate of the acidic salt, more preferably a hydrate of the hydrochloride, and still more preferably a dihydrate of the hydrochloride.

The present production method can also be carried out by adding an amino acid to a suspension or solution of the acidic salt of the compound A or the hydrate thereof, and a method in which an amino acid is added to the solution of the acidic salt of the compound A or the hydrate thereof is preferable.

Specifically, the present production method can be carried out in such a manner that the acidic salt of the compound A or the hydrate thereof is added to an acidic solvent, and, if necessary, heated to prepare an acidic salt solution of the compound A, and an amino acid is added to the resulting solution.

The reaction temperature in the present production method is preferably 15° C. to 60° C. and more preferably 40° C. to 50° C.

The reaction time in the present production method is, for example, preferably 1 minute to 24 hours and more preferably 30 minutes to 6 hours.

The reaction atmosphere is not particularly limited, but the reaction is preferably carried out in an inert gas atmosphere. Examples of the inert gas atmosphere include an argon atmosphere and a nitrogen atmosphere.

In the present production method, a seed crystal may be added as necessary.

The seed crystal may be, for example, a part of a crystal produced in the same manner as in the method described in Example 12 (2) of WO2013/047758A, or may be a part of a crystal produced by the production method according to the embodiment of the present invention.

In a case where the compound A•¾ hydrate obtained by the production method according to the embodiment of the present invention is used as a medicine, usually, pharmaceutical aids such as an excipient, a carrier, and a diluent used for formulation may be appropriately mixed. These pharmaceutical aids can be administered orally or parenterally in the form of a tablet, a capsule, a powder, a syrup, a granule, a pill, a suspension, an emulsion, a solution, a powdery preparation, a suppository, an eye drop, a nasal drop, an ear drop, a patch, an ointment, or an injection according to a conventional method. In addition, the administration method, dosage, and number of administrations can be appropriately selected according to the age, weight, and condition of the patient. Usually, for an adult, 0.01 mg/kg/day to 1000 mg/kg/day may be administered singly or in divided doses by oral or parenteral administration (for example, injection, drip infusion, or rectal administration).

The form of the preparation is preferably a tablet. For example, the form, production method, additives, description, and the like of tablets described in WO2014/112530A (US2015/0057324A) can be incorporated and referred to, the contents of which are incorporated herein.

A preferred tablet contains the compound A•¾ hydrate, silicon dioxide, and crystalline cellulose. Addition of crystalline cellulose can prevent capping of the tablet from peeling off in the form of a cap.

In a case where crystalline cellulose is added, the content of crystalline cellulose is preferably 0.1% by mass to 20% by mass, more preferably 1% by mass to 15% by mass, still more preferably 2% by mass to 12% by mass, and most preferably 3% by mass to 10% by mass of the tablet mass.

In a case where crystalline cellulose is added, the content of the compound A•¾ hydrate is preferably 60% by mass to 80% by mass and more preferably 65% by mass to 75% by mass of the tablet mass.

The above-mentioned tablet may further contain other additives described in WO2014/112530A, and for the types and amounts suitable as additives, the description in WO2014/112530A can be incorporated and referred to.

The usefulness of the present invention will be illustrated by the following Examples.

EXAMPLES

The present invention will be described with reference to Reference Examples, Examples, and Comparative Examples, but the present invention is not limited thereto. Unless otherwise specified, "%" means "% by mass".

An infrared absorption spectrum (hereinafter, referred to as IR) was measured by an attenuated total reflection method (ATR method).

The moisture content was measured by the Karl Fischer method.

The seed crystals used in Examples and Comparative Examples were produced in the same manner as in the method described in WO2013/047758A.

Reference Example 1

In the same manner as in the method described in Example 9 (1) of WO2013/047758A, 16.4 g of 5-hydroxy-1H-imidazole-4-carboxamide hydrochloride dihydrate was obtained as pale yellow crystals, using 10.0 g of 2-aminomalonamide.

Reference Example 2

In the same manner as in the method described in Example 12 (1) of WO2013/047758A, 13.9 g of 5-hydroxy-1H-imidazole-4-carboxamide hydrochloride dihydrate was obtained as pale yellow crystals, using 15.0 g of 5-hydroxy-1H-imidazole-4-carboxamide hydrochloride dihydrate.

Example 1

Under a nitrogen atmosphere, 10.0 g of 5-hydroxy-1H-imidazole-4-carboxamide hydrochloride dihydrate produced according to the method described in Reference Example 2 was added to 120 mL of 0.45 mol/L hydrochloric acid which was then heated to 47° C. to dissolve the compound. To the resulting solution was added dropwise 10 mL of a 1.5 mol/L monopotassium dihydrogen phosphate aqueous solution at 46° C. to 47° C. To the resulting solution was added 50 mg of 5-hydroxy-1H-imidazole-4-carboxamide·¾ hydrate as a seed crystal, followed by stirring at 46° C. to 48° C. for 30 minutes. After confirming the precipitation of crystals of the reaction mixture, 60 mL of a 1.5 mol/L monopotassium dihydrogen phosphate aqueous solution was added dropwise to the solution at 47° C. to 48° C. The reaction mixture was cooled to 0° C. and then stirred for 1 hour, and the precipitated crystals were collected by filtration.

The obtained crystals were divided into two parts, and one part of the crystals was air-dried to obtain 3.23 g of an unwashed product of 5-hydroxy-1H-imidazole-4-carboxamide·¾ hydrate as white crystals.

The other part of the crystals was sequentially washed with a mixed solution of 5.0 mL of acetone and 10.0 mL of water and 15.0 mL of acetone, and then air-dried to obtain 2.94 g of a washed product of 5-hydroxy-1H-imidazole-4-carboxamide·¾ hydrate as white crystals. Each IR was consistent.

Moisture content: unwashed product: 9.8%, washed product: 8.8%

IR (cm$^{-1}$): 3437, 1618, 1587, 1436

Example 2

In the same manner as in Example 1, 3.33 g of an unwashed product and 3.06 g of a washed product of 5-hydroxy-1H-imidazole-4-carboxamide·¾ hydrate were obtained as white crystals, using 40 mL of a 1.5 mol/L dipotassium hydrogen phosphate aqueous solution as a base. Each IR was consistent with the IR of Example 1.

Example 3

In the same manner as in Example 1, 3.22 g of an unwashed product and 3.11 g of a washed product of 5-hydroxy-1H-imidazole-4-carboxamide·¾ hydrate were obtained as white crystals, using 60 mL of a 0.5 mol/L potassium phosphate aqueous solution as a base. Each IR was consistent with the IR of Example 1.

Example 4

In the same manner as in Example 1, 3.54 g of an unwashed product and 2.37 g of a washed product of 5-hydroxy-1H-imidazole-4-carboxamide·¾ hydrate were obtained as white crystals, using 205 mL of a 1.5 mol/L sodium dihydrogen phosphate aqueous solution as a base. Each IR was consistent with the IR of Example 1.

Example 5

In the same manner as in Example 1, 3.00 g of an unwashed product and 3.56 g of a washed product of 5-hydroxy-1H-imidazole-4-carboxamide·¾ hydrate were obtained as white crystals, using 80 mL of a 0.75 mol/L disodium hydrogen phosphate aqueous solution as a base. Each IR was consistent with the IR of Example 1.

Example 6

In the same manner as in Example 1, 3.21 g of an unwashed product and 3.16 g of a washed product of 5-hydroxy-1H-imidazole-4-carboxamide·¾ hydrate were obtained as white crystals, using 60 mL of a 0.5 mol/L sodium phosphate aqueous solution as a base. Each IR was consistent with the IR of Example 1.

Example 7

Under a nitrogen atmosphere, 10.0 g of 5-hydroxy-1H-imidazole-4-carboxamide hydrochloride dihydrate produced according to the method described in Reference Example 2 was added to 120 mL of 0.45 mol/L hydrochloric acid which was then heated to 47° C. to dissolve the compound. To the resulting solution was added dropwise 10 mL of a 1.5 mol/L β-alanine aqueous solution at 46° C. to 47° C. To the resulting solution was added 50 mg of 5-hydroxy-1H-imidazole-4-carboxamide·¾ hydrate as a seed crystal, followed by stirring at 46° C. to 47° C. for 40 minutes. After confirming the precipitation of crystals of the reaction mixture, 50 mL of a 1.5 mol/L β-alanine aqueous solution was added dropwise at 46° C. to 48° C. The reaction mixture was cooled to 0° C. and then stirred for 1 hour and 40 minutes, and the precipitated crystals were collected by filtration.

The obtained crystals were divided into two parts, and one part of the crystals was air-dried to obtain 3.52 g of an unwashed product of 5-hydroxy-1H-imidazole-4-carboxamide·¾ hydrate as white crystals.

The other part of the crystals was sequentially washed with a mixed solution of 5.0 mL of acetone and 10.0 mL of water and 15.0 mL of acetone, and then air-dried to obtain 2.65 g of a washed product of 5-hydroxy-1H-imidazole-4-carboxamide·¾ hydrate as white crystals. Each IR was consistent.

Moisture content: unwashed product: 9.1%, washed product: 8.5%

IR (cm$^{-1}$): 3438, 1616, 1587, 1436

Example 8

In the same manner as in Example 7, 3.28 g of an unwashed product and 3.15 g of a washed product of 5-hydroxy-1H-imidazole-4-carboxamide•¾ hydrate were obtained as white crystals, using 68 mL of a 1.5 mol/L L-alanine aqueous solution as a base. Each IR was consistent with the IR of Example 7.

Example 9

In the same manner as in Example 7, 3.29 g of an unwashed product and 3.18 g of a washed product of 5-hydroxy-1H-imidazole-4-carboxamide•¾ hydrate were obtained as white crystals, using 65 mL of a 1.5 mol/L L-serine aqueous solution as a base. Each IR was consistent with the IR of Example 7.

Example 10

In the same manner as in Example 7, 3.18 g of an unwashed product and 2.94 g of a washed product of 5-hydroxy-1H-imidazole-4-carboxamide•¾ hydrate were obtained as white crystals, using 105 mL of a 1.25 mol/L L-threonine aqueous solution as a base. Each IR was consistent with the IR of Example 7.

Example 11

In the same manner as in Example 7, 3.18 g of an unwashed product and 3.10 g of a washed product of 5-hydroxy-1H-imidazole-4-carboxamide•¾ hydrate were obtained as white crystals, using 70 mL of a 1.5 mol/L glycine aqueous solution as a base. The IR was consistent with the IR of Example 7.

Example 12

In the same manner as in Example 7, 3.20 g of an unwashed product and 3.14 g of a washed product of 5-hydroxy-1H-imidazole-4-carboxamide•¾ hydrate were obtained as white crystals, using 130 mL of a 1.5 mol/L L-cysteine aqueous solution as a base. Each IR was consistent with the IR of Example 7.

Comparative Example 1

In the same manner as in the method described in Example 12 (2) of WO2013/047758A, using 10.0 g of 5-hydroxy-1H-imidazole-4-carboxamide hydrochloride dihydrate, crystals precipitated from the reaction mixture were collected by filtration.

The obtained crystals were divided into two parts, and one part of the crystals was air-dried to obtain 3.29 g of an unwashed product of 5-hydroxy-1H-imidazole-4-carboxamide•¾ hydrate as white crystals.

The other part of the crystals was sequentially washed with a mixed solution of 5.0 mL of acetone and 10.0 mL of water and 15.0 mL of acetone, and then air-dried to obtain 3.31 g of a washed product of 5-hydroxy-1H-imidazole-4-carboxamide•¾ hydrate as white crystals. The IR was consistent with the IR of Example 1.

Comparative Example 2

Under a nitrogen atmosphere, 10.0 g of 5-hydroxy-1H-imidazole-4-carboxamide hydrochloride dihydrate produced according to the method described in Reference Example 2 was added to 120 mL of 0.45 mol/L hydrochloric acid which was then heated to 47° C. to dissolve the compound. To the resulting solution was added dropwise 5.0 mL of a 3.0 mol/L potassium formate solution at 46° C. to 47° C. To the resulting solution was added 50 mg of 5-hydroxy-1H-imidazole-4-carboxamide•¾ hydrate as a seed crystal, followed by stirring at 47° C. to 48° C. for 2 hours and 15 minutes. After confirming the precipitation of crystals of the reaction mixture, a 3.0 mol/L potassium formate solution was added dropwise at 47° C. to 48° C. The reaction mixture was cooled to 0° C. and then the crystals were collected by filtration.

The obtained crystals were divided into two parts, and one part of the crystals was air-dried to obtain 3.35 g of an unwashed product of 5-hydroxy-1H-imidazole-4-carboxamide•¾ hydrate as white crystals.

The other part of the crystals was washed with a mixed solution of 5.0 mL of acetone and 10.0 mL of water and with 15.0 mL of acetone, and then air-dried to obtain 3.29 g of a washed product of 5-hydroxy-1H-imidazole-4-carboxamide•¾ hydrate as white crystals. The IR was consistent with the IR of Example 1.

Formulation Example 1

39.46 g of lactose hydrate (Pharmatose 200M, manufactured by DMV-Fonterra Excipients GmbH & Co. KG), 32.01 g of carmellose calcium (ECG-505, manufactured by Nichirin Chemical Industries, Ltd.), and 20.01 g of crystalline cellulose (KG-1000, manufactured by Asahi Kasei Corporation) were added to 276.59 g of 5-hydroxy-1H-imidazole-4-carboxamide•¾ hydrate to obtain a mixture. 12.00 g of hydroxypropyl cellulose (HPC-L, manufactured by Nippon Soda Co., Ltd.) was dissolved in 456.00 g of water, and 12.00 g of light anhydrous silicic acid (AEROSIL-200, manufactured by Nippon Aerosil Co., Ltd.) was further dispersed therein to prepare an aqueous solution. The prepared aqueous solution was sprayed on the obtained mixture which was then granulated by a fluidized bed granulator (FD-MP-01, manufactured by Powrex Corporation) and dried to obtain a granulated powder. 7.35 g of magnesium stearate (manufactured by Merck & Co.) sieved through a 180 μm sieve was added to 360.38 g of the obtained granulated powder, followed by mixing in a V-type mixer (Mixer S-5 type, manufactured by Tsutsui Scientific Instruments Co., Ltd.) at 30 rpm for 60 minutes to obtain a mixed powder. The obtained mixed powder was tableted at a tableting pressure of 10 kN by a rotary tableting machine (PICCOLA B-10, manufactured by Riva S.A.) using a double radius (12R×3R mm) punch having a tablet diameter of 8.5 mm to obtain round uncoated tablet weighing 320 mg per tablet. The tablet hardness of the uncoated tablet was 76 N as a result of measurement using a tablet hardness tester 8M (manufactured by Dr. Schleuniger Pharmatron AG).

The obtained uncoated tablets were coated with a coating agent (OPADRY 03A470001 TAN (hypromellose 2910: 60.00%, talc: 20.00%, titanium oxide: 18.86%, yellow iron sesquioxide: 1.00%, black iron oxide: 0.14%), manufactured by Colorcon Japan LLC.) at a ratio of 12 mg per tablet with a coating machine (DRC-200, manufactured by Powrex Corporation) to obtain round film-coated tablets.

The usefulness of the present invention will be illustrated by the following Test Examples.

A washed product and an unwashed product of the compound A·¾ hydrate obtained in each of Reference Examples, Examples, or Comparative Examples were used in each Test Example.

Test Example 1 (Test of Coloring Stability During Storage)

The compound A·¾ hydrate (washed product) obtained in each of Examples 1 to 12 was used as a test substance.

About 1 g of the test substance was placed in a storage bag formed by stacking two 0.04 mm-thick polyethylene bags, sealed in each polyethylene bag, and stored for 5 days in an air atmosphere under the conditions of light shielding, 60° C., and 75% relative humidity.

The tone of the test substance after the test was visually observed. In addition, a change in the color of the crystal before and after the test was measured with a spectrophotometric color difference meter to determine the color difference.

The results are shown in Table 1.

Colorimeter: spectrophotometric color difference meter SE2000 manufactured by Nippon Denshoku Industries Co., Ltd.

Measurement method: reflection method

TABLE 1

| Test substance | Base used | Tone | Color difference (ΔE) |
|---|---|---|---|
| Example 1 | Potassium dihydrogen phosphate | White | 1.8 |
| Example 2 | Dipotassium hydrogen phosphate | White | 2.6 |
| Example 3 | Tripotassium phosphate | White | 2.0 |
| Example 4 | Sodium dihydrogen phosphate | White | 2.7 |
| Example 5 | Disodium hydrogen phosphate | White | 3.6 |
| Example 6 | Trisodium phosphate | White | 5.2 |
| Example 7 | β-alanine | White | 2.9 |
| Example 8 | L-alanine | White | 4.2 |
| Example 9 | L-serine | White | 5.0 |
| Example 10 | L-threonine | White | 3.7 |
| Example 11 | L-glycine | White | 5.3 |
| Example 12 | L-cysteine | White | 1.0 |

The compounds of Examples 1 to 12 were all white in tone after the acceleration test, had a color difference (ΔE) of 6 or less before and after the acceleration test, and were excellent in coloring stability during storage.

Test Example 2

The compound A·¾ hydrate (washed product) of each of Examples 1 to 12 and Comparative Examples 1 and 2 was used as a test substance.

The quality of the compound A·¾ hydrate was evaluated by HPLC measurement. The quantification was determined by HPLC area %.

Figure 1:
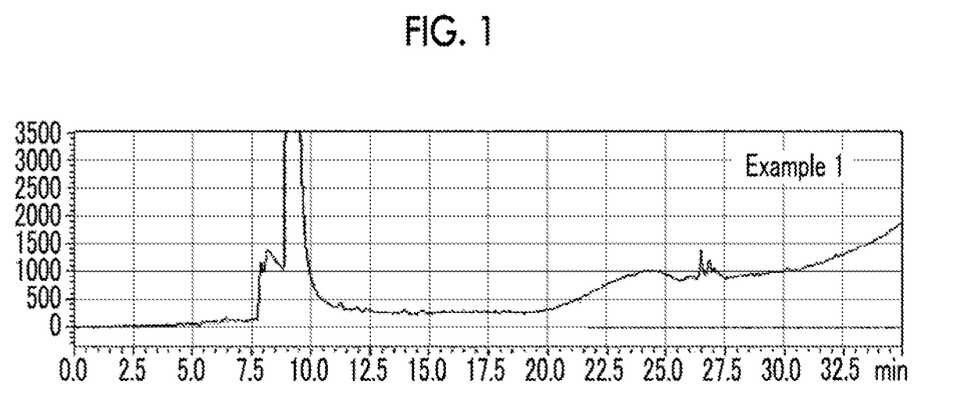
FIG. 1 is a chart of HPLC measurement results of Example 1 of Test Example 2.
Figure 2:
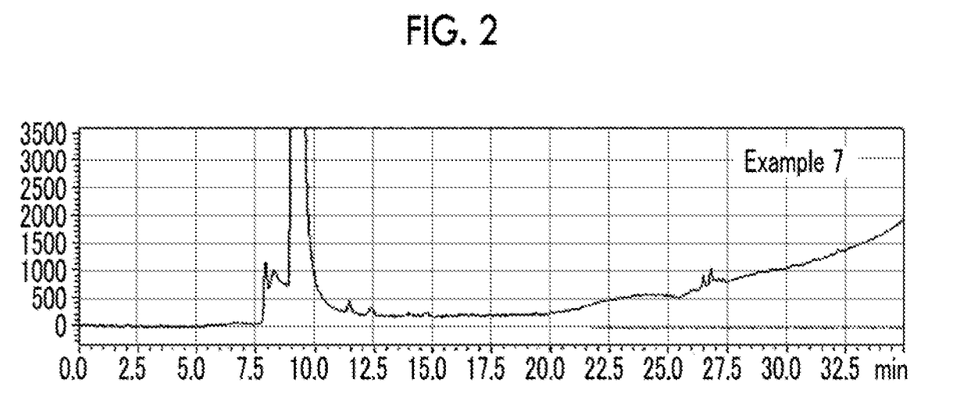
FIG. 2 is a chart of HPLC measurement results of Example 7 of Test Example 2.
Figure 3:
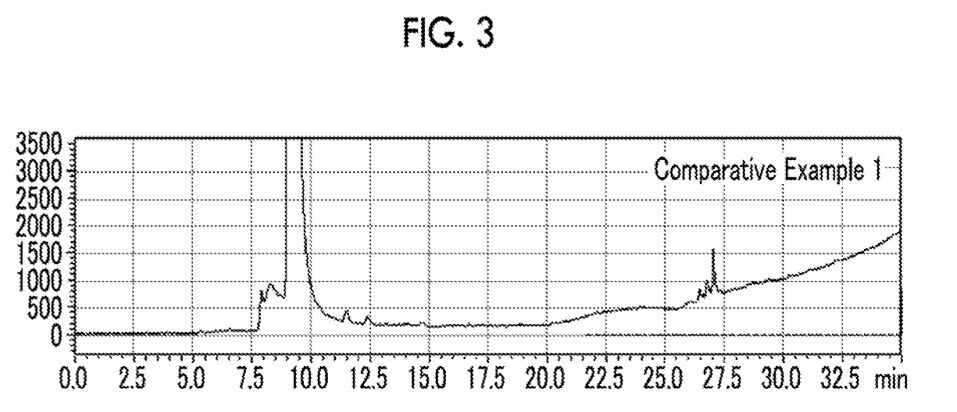
FIG. 3 is a chart of HPLC measurement results of Comparative Example 1 of Test Example 2.
Figure 4:
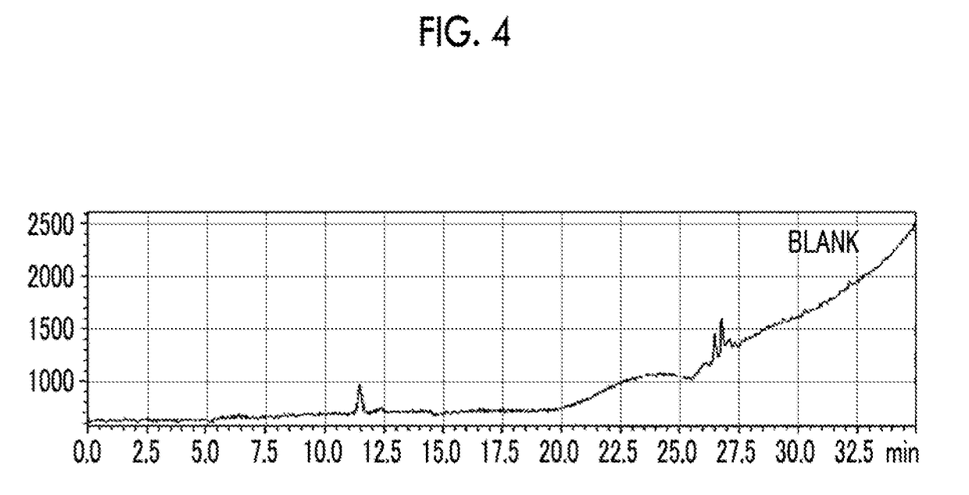
FIG. 4 is a chart of HPLC measurement results of a blank of Test Example 2.
Figure 5:
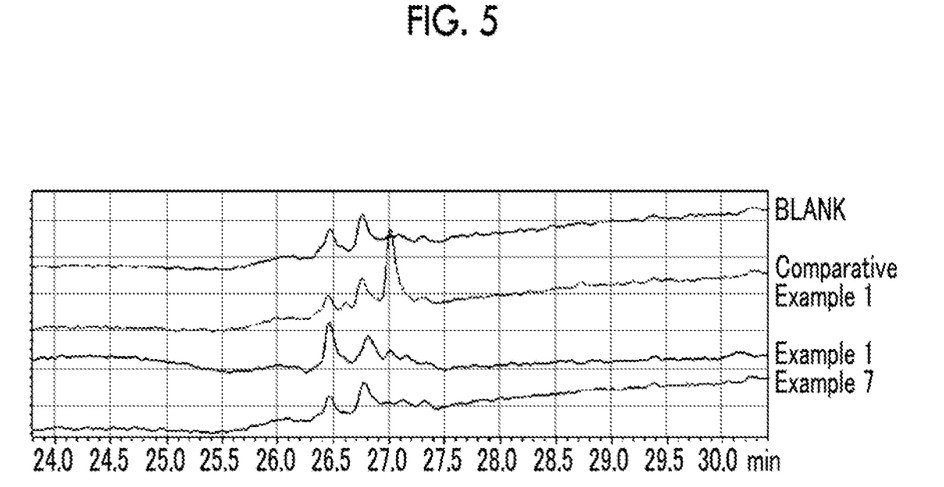
FIG. 5 is an enlarged chart obtained by superimposing a retention time of about 27.0 minutes on a chart of HPLC measurement results of Example 1, Example 7, Comparative Example 1, and blank of Test Example 2.

The results are shown in Table 2 and FIGS. 1 to 5.

HPLC equipment: Prominence system (manufactured by Shimadzu Corporation)

HPLC measurement conditions

Column: 6.0×250 mm Hydrosphere C18, particle size: 5 μm (manufactured by YMC Co., Ltd.)

Measurement wavelength: 220 nm

Column temperature: 30° C.

Mobile phase A: 0.1% phosphoric acid/water

Mobile phase B: 0.1% phosphoric acid/acetonitrile

Gradient conditions:
0 to 10 minutes: mobile phase B 0%
10 to 30 minutes: mobile phase B 0%→50% (linear gradient)
30 to 35 minutes: mobile phase B 50%

Flow rate: 0.75 mL/min

Injection volume: 10 μL

TABLE 2

| Test substance | Base used | Amount (%) of impurities having retention time of 27.0 minutes |
|---|---|---|
| Example 1 | Potassium dihydrogen phosphate | Not detected |
| Example 2 | Dipotassium hydrogen phosphate | Not detected |
| Example 3 | Tripotassium phosphate | Not detected |
| Example 4 | Sodium dihydrogen phosphate | Not detected |
| Example 5 | Disodium hydrogen phosphate | Not detected |
| Example 6 | Trisodium phosphate | Not detected |
| Example 7 | β-alanine | Not detected |
| Example 8 | L-alanine | Not detected |
| Example 9 | L-serine | Not detected |
| Example 10 | L-threonine | Not detected |
| Example 11 | L-glycine | Not detected |
| Example 12 | L-cysteine | Not detected |
| Comparative Example 1 | Sodium formate | 0.03 |
| Comparative Example 2 | Potassium formate | 0.03 |

The compounds of Examples 1 to 12 and Comparative Examples 1 and 2 each had a purity of 99.9% or more.

On the other hand, the compounds of Examples 1 to 12 did not contain the component having a retention time of 27.0 minutes contained in the compounds of Comparative Examples 1 and 2. The 5-hydroxy-1H-imidazole-4-carboxamide·¾ hydrate obtained by the production method according to the embodiment of the present invention was higher in purity than Comparative Examples 1 and 2.

Test Example 3

The compound A·¾ hydrate (unwashed product) obtained in each of Examples 1 to 12 and Comparative Examples 1 and 2 was used as a test substance.

The test was carried out in the same manner as in Test Example 1.

The results are shown in Table 3.

TABLE 3

| Test substance | Base used | Tone | Color difference (ΔE) |
|---|---|---|---|
| Example 1 | Potassium dihydrogen phosphate | White | 1.6 |
| Example 2 | Dipotassium hydrogen phosphate | White | 3.1 |
| Example 3 | Tripotassium phosphate | White | 1.1 |
| Example 4 | Sodium dihydrogen phosphate | White | 2.3 |
| Example 5 | Disodium hydrogen phosphate | White | 4.1 |
| Example 6 | Trisodium phosphate | White | 2.3 |
| Example 7 | β-alanine | White | 1.0 |
| Example 8 | L-alanine | White | 1.4 |
| Example 9 | L-serine | White | 0.9 |

TABLE 3-continued

| Test substance | Base used | Tone | Color difference (ΔE) |
|---|---|---|---|
| Example 10 | L-threonine | White | 2.2 |
| Example 11 | L-glycine | White | 1.6 |
| Example 12 | L-cysteine | White | 2.9 |
| Comparative Example 1 | Sodium formate | Black blue | 62.4 |
| Comparative Example 2 | Potassium formate | Black blue | 51.4 |

Compared with the compound A•¾ hydrate (unwashed product) of Comparative Examples 1 and 2, the compound A•¾ hydrate (unwashed product) of Examples 1 to 12 had a smaller color difference before and after the test and significantly improved coloring stability during storage.

That is, the compound A•¾ hydrate obtained by the production method according to the embodiment of the present invention has a feature that the compound is less likely to be colored even in a case where the solvent used for the crystallization in the final step remains.

The disclosure of JP2017-208570 filed on Oct. 27, 2017 is incorporated herein by reference in its entirety.

All publications, patent applications, and technical standards mentioned in this specification are herein incorporated by reference to the same extent as if each individual publication, patent application, and technical standard was specifically and individually indicated to be incorporated by reference.

The compound A•¾ hydrate obtained by the production method according to the embodiment of the present invention has characteristics such as excellent coloring stability during storage and high purity.

Furthermore, the compound A•¾ hydrate obtained by the production method according to the embodiment of the present invention has a feature that the compound is less likely to be colored even in a case where the solvent used for the crystallization in the final step remains.

The production method according to the embodiment of the present invention is useful as an industrial production method of 5-hydroxy-1H-imidazole-4-carboxamide•¾ hydrate.

What is claimed is:

1. A method for producing a 5-hydroxy-1H-imidazole-4-carboxamide•¾ hydrate, comprising:
    reacting an acidic salt of 5-hydroxy-1H-imidazole-4-carboxamide or a hydrate thereof with a base selected from the group consisting of a phosphate and an amino acid in the presence of an acidic solvent to obtain a 5-hydroxy-1H-imidazole-4-carboxamide•¾ hydrate.
2. The production method according to claim 1, wherein the base is a phosphate.
3. The production method according to claim 1, wherein the base is an alkali metal salt of phosphoric acid.
4. The production method according to claim 1, wherein the base is dipotassium hydrogen phosphate.
5. The production method according to claim 1, wherein the base is an amino acid.
6. The production method according to claim 1, wherein the base is an amino acid selected from the group consisting of an acidic amino acid and a neutral amino acid.
7. The production method according to claim 1, wherein the base is a neutral amino acid.
8. The production method according to claim 1, wherein the base is serine, alanine, β-alanine, threonine, glycine, or cysteine.
9. The production method according to claim 1, wherein the base is alanine, β-alanine, threonine, or cysteine.
10. The production method according to claim 1, wherein the acidic salt is a hydrate of a hydrochloride.
11. The production method according to claim 1, wherein the acidic solvent is aqueous hydrochloric acid.

* * * * *